(12) United States Patent
Ide et al.

(10) Patent No.: US 8,690,788 B2
(45) Date of Patent: Apr. 8, 2014

(54) LIVING BODY INFORMATION MEASURING APPARATUS

(75) Inventors: Kazuhiro Ide, Takatsuki (JP); Manabu Hamamoto, Moriyama (JP); Nobuo Iwai, Hikone (JP)

(73) Assignee: Panasonic Corporation, Osaka (JP)

( * ) Notice: Subject to any disclaimer, the term of this patent is extended or adjusted under 35 U.S.C. 154(b) by 1297 days.

(21) Appl. No.: 12/093,990

(22) PCT Filed: Nov. 15, 2006

(86) PCT No.: PCT/JP2006/322766
§ 371 (c)(1),
(2), (4) Date: May 16, 2008

(87) PCT Pub. No.: WO2007/060870
PCT Pub. Date: May 31, 2007

(65) Prior Publication Data
US 2009/0163824 A1    Jun. 25, 2009

(30) Foreign Application Priority Data

Nov. 22, 2005  (JP) ................................. 2005-337571

(51) Int. Cl.
*A61B 5/02* (2006.01)
(52) U.S. Cl.
USPC ............ 600/499; 600/492; 600/491; 600/503
(58) Field of Classification Search
USPC .................. 600/499, 492, 503, 504, 490, 491
See application file for complete search history.

(56) References Cited

U.S. PATENT DOCUMENTS 5,069,219 A * 12/1991 Knoblich ...................... 600/492
5,183,050 A * 2/1993 Kawamura ..................... 600/500
(Continued)

FOREIGN PATENT DOCUMENTS

EP    1125551    8/2001
EP    1442701    8/2004
(Continued)

OTHER PUBLICATIONS

Machine translation of JP 2003-290156.*
(Continued)

*Primary Examiner* — Michael Kahelin
*Assistant Examiner* — Tho Tran
(74) *Attorney, Agent, or Firm* — Greenblum & Bernstein, P.L.C.

(57) ABSTRACT

A living body information measuring apparatus can suppress the bulge of tendons due to the bending of a wrist or fingers, and has good contact intimacy with arteries, making it possible to make accurate measurements of living body information. A cuff is formed of: a compression fluid bag which is provided for detecting a pulse wave signal, and which can be expanded and contracted by being supplied with a fluid; and two auxiliary fluid bags which are provided on an outer side of the compression fluid bag, and which can be expanded and contracted by being supplied with the fluid. The auxiliary fluid bags have a two-layer structure, and are connected to the compression fluid bag via opening portions, while the auxiliary fluid bags are respectively divided from each other. The compression fluid bag compresses the tendons, the radial artery and the ulnar artery, while the auxiliary fluid bag and the auxiliary fluid bag compress the radial artery and the ulnar artery, respectively. Thus, the bulge of the tendons due to the bending of the wrist and fingers can be suppressed, so that the contact intimacy of the compression fluid bag and the auxiliary fluid bags with the wrist is not hindered.

10 Claims, 10 Drawing Sheets

(56) References Cited

U.S. PATENT DOCUMENTS

| | | |
|---|---|---|
| 6,694,821 B2 | 2/2004 | Yamakoshi et al. |
| 2001/0016692 A1 | 8/2001 | Itonaga et al. |
| 2002/0170359 A1 | 11/2002 | Yamakoshi et al. |
| 2002/0183667 A1 | 12/2002 | Kitadou et al. |
| 2004/0193059 A1 | 9/2004 | Inoue et al. |
| 2005/0182332 A1 | 8/2005 | Sano et al. |
| 2005/0187485 A1 | 8/2005 | Fumuro et al. |
| 2006/0135873 A1* | 6/2006 | Karo et al. .................. 600/499 |

FOREIGN PATENT DOCUMENTS

| | | |
|---|---|---|
| JP | 2003-24286 | 1/2003 |
| JP | 2003-290156 | 10/2003 |
| JP | 2005-230175 | 9/2005 |

OTHER PUBLICATIONS

English language Abstract of JP 2003-290156, Oct. 14, 2003.

English language Abstract of JP 2003-24286, Jan. 28, 2003.

English language Abstract of JP 2005-230175, Sep. 2, 2005.

Search report from E.P.O., mail date is Sep. 26, 2011.

* cited by examiner

PRIOR ART

FIG. 15

PRIOR ART

LIVING BODY INFORMATION MEASURING APPARATUS

TECHNICAL FIELD

The present invention relates to a living body information measuring apparatus for measuring information of a living body such as blood pressure, heart beat and pulse wave, and more particularly to a structure of a cuff for measuring blood pressure.

BACKGROUND ART

In the prior art, there is a known living body information measuring apparatus which, for measurement, compresses a part such as wrist, upper arm, finger or ankle by using a fluid bag supplied with a fluid such as air. A known blood pressure monitor uses the oscillometric method to measure the blood pressure. In the oscillometric method, a fluid bag is first wrapped around a tissue of a living body, and fixed. Then, either while a pressure is applied to the tissue of the living body by feeding the fluid into the fluid bag until the arteries of the tissue of the living body are completely occluded, and thereafter the pressure of the fluid bag is gradually reduced at a constant rate, or while the pressure of the fluid bag is increased by feeding the fluid thereinto at a constant rate until the arteries of the tissue of the living body are completely occluded, the method uses a sensor to detect a pulse wave signal of the arteries superimposed on the pressure of the fluid bag, and measures systolic and diastolic blood pressures thereof based on the amplitude variation of this signal by using a predetermined algorithm. Thus, this method needs to compress the arteries at a predetermined pressure so as to accurately detect a change in the arteries Now, multiple arteries are present in a living body part such as wrist, finger and ankle. For example, two arteries, radial artery and ulnar artery, are present on the palm side of the wrist, and three arteries are present in the ankle, while two arteries and one artery are present on the palm side and on the dorsal side of a finger, respectively. Further, various bones, muscles and tendons are present near these arteries and are involved in the movement of the living body parts. For example, a long palmar muscle, a flexor carpi radialis tendon, a flexor carpi ulnaris tendon, a flexor digitorum superficialis tendon and a flexor digitorum profundus tendon are present on the palm side of the wrist. Wrist bending is produced by the contraction of the long palmar muscle and the flexor carpi radialis tendon. On the other hand, finger bending is produced by the contraction of the flexor digitorum superficialis tendon and the flexor digitorum profundus tendon. Thus, the living body parts have complex structures.

When a wrist or a finger is bent as described above, tendons present on the surface of the wrist bulge, and the tendons become tense and tight. Therefore, if the above-described method is used to measure blood pressure, the bulged tendons may, in some cases, hinder the compression on the arteries as applied by the fluid bag, and there is a possibility that contact intimacy between the fluid bag and the living body part may become poor. Thus, there may be a case where the arteries cannot be occluded unless the pressure of the fluid bag is set higher than a predetermined pressure, leading to a problem that a reduction in the detectability of a pulse wave signal of the arteries is likely to cause measurement errors.

Figure 14:
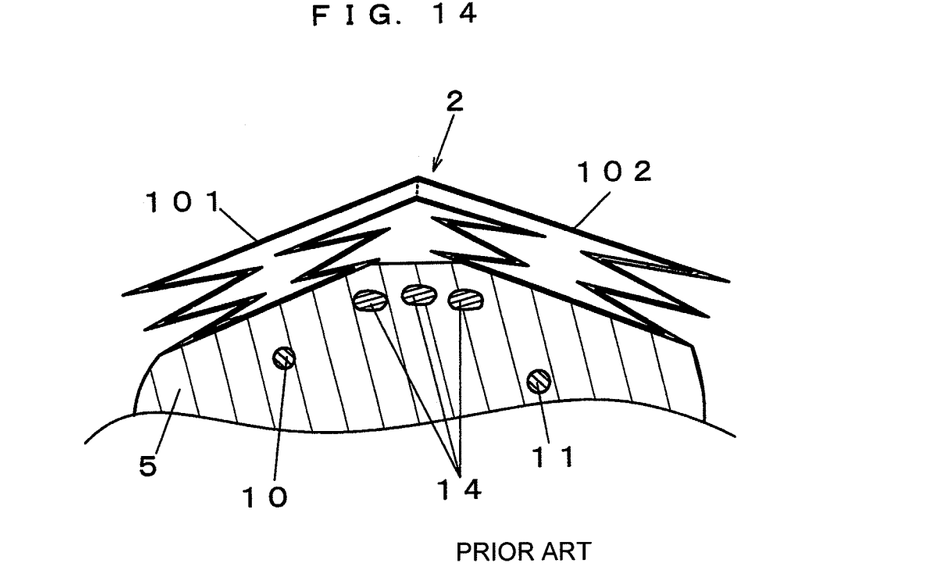
FIG. 14 is a cross-sectional view showing a state where a conventional blood pressure monitor cuff compresses a wrist.

Thus, as described e.g. in Japanese Patent (sic, correctly: Japanese Patent Publication) 2003-290156, a blood pressure monitor is proposed in which a cuff to compress the arteries is formed by a plurality of fluid bags corresponding in number and positions to the respective arteries, and in which these fluid bags are connected to each other, each having a stacked structure in the direction of compressing the artery. FIG. 14 shows a cross-sectional view in a state where the cuff of the blood pressure monitor compresses a wrist. Note that only a wrist 5 and a cuff 2 are shown for convenience, omitting the showing of a main body of the blood pressure monitor and others.

The wrist 5 is composed e.g. of a radial artery 10, an ulnar artery 11, and tendons 14 which are related to the movements of the wrist 5 and fingers. The cuff 2 has fluid bags 101, 102 divided left and right with the tendons 14 therebetween, in which the fluid bag 101 and the fluid bag 102 respectively compress the radial artery 10 and the ulnar artery 11. The cuff 2 having such a structure can measure accurate living body information because the respective fluid bags 101, 102 compress the radial artery 10 and the ulnar artery 11.

However, the compression force of the fluid bags 101, 102 to the tendons 14 is weak, so that the bulge of the tendons 14 due to e.g. the bending of the wrist 5 may not be suppressed in some cases. Therefore, if the tendons 14 bulge, the contact intimacy between the cuff 2 and the wrist 5 becomes poor, so that the compression force to the radial artery 10 and the ulnar artery 11 becomes weak. Thus, there may be a case where the radial artery 10 and the ulnar artery 11 cannot be occluded, unless the pressure of the fluid bags 101, 102 is set higher than a predetermined pressure. As a result, this may cause measurement errors in some cases.

Further, if a user attaches the blood pressure monitor at a position shifted around the wrist 5 from a predetermined position, the contact intimacy of the fluid bags 101, 102 with the radial artery 10 and the ulnar artery 11 becomes weak. This weakens the compression force to the radial artery 10 and the ulnar artery 11, which may cause measurement errors in some cases. In order to prevent this, a method is known in which a hard clip board or the like is provided inside the cuff 2. However, this has a problem that it is difficult for the user to attach it. Further, if the wrist or the fingers are bent inward or bent outward, the intimate contact state of the fluid bags 101, 102 with the radial artery 10 and the ulnar artery 11 changes, thereby causing a change in the compression state. Thus, it is required to provide a control jig for controlling the postures of the wrist and fingers, reducing the portability of such blood pressure monitor. In addition, in order to prevent the user from bending the wrist or fingers inward, it is required to limit its posture for measurement, which may, in some cases, force the user to perform measurements in an unnatural posture.

Figure 15:
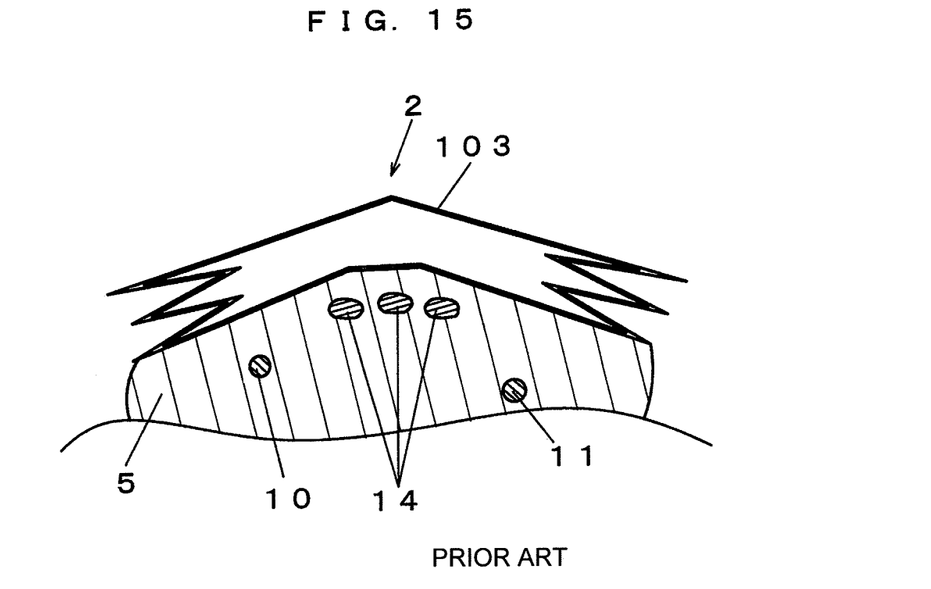
FIG. 15 is a cross-sectional view showing a state where a modified example of the conventional blood pressure monitor cuff compresses a wrist.

Further, as described in Japanese Patent (sic, correctly: Japanese Patent Publication) 2003-24286, a blood pressure monitor is proposed in which a cuff is formed of a fluid bag which is not divided left and right. FIG. 15 shows a cross-sectional view in a state where the cuff of the blood pressure monitor compresses a wrist. Note that only a wrist 5 and a cuff 2 are shown for convenience, omitting the showing of a main body of the blood pressure monitor and others. The cuff 2 has a substantially circular-shaped fluid bag 103 to cover the wrist 5. The fluid bag 103 compresses the wrist 5 regardless of the presence of tendons 14.

The fluid bag 103 has a substantially circular-shaped cross section, so that it generally has a property that its central portion expands most while an expansion of its side portions is small. Thus, the compression force of the fluid bag 103 to the tendons 14 is strong to be able to suppress the bulge of the tendons 14 due to the bending of the wrist or fingers. However, the contact intimacy of the fluid bag 103 with the radial artery 10 and the ulnar artery 11 is weak, causing the compression force to be weak, which may cause measurement errors in some cases.

DISCLOSURE OF INVENTION

An object of the present invention, to solve the problems described above, is to provide a living body information measuring apparatus which can suppress the bulge of tendons due to the bending of a wrist or fingers, and has good contact intimacy with arteries, and which can make accurate measurements of living body information.

In order to achieve the above object, the present invention provides a living body information measuring apparatus using a fluid bag to compress a living body and using a sensor to detect a change in multiple arteries present in a tissue of the living body for measuring living body information, wherein the fluid bag comprises: a compression fluid bag which contacts the living body to measure the living body information from the arteries, and which can be expanded and contracted by being supplied with a fluid; and at least two independent auxiliary fluid bags which are provided on an outer side of the compression fluid bag relative to the living body, and which can be expanded and contracted by being supplied with the fluid, and wherein the auxiliary fluid bags are respectively divided from each other.

According to such a structure, the compression fluid bag contacts the living body to measure the living body information from the arteries, and the at least two auxiliary fluid bags are respectively divided from each other, so that it can compress the respective arteries. Thus, in such a tissue of the living body that a tight tissue such as tendons is present at a substantially central portion with arteries on both sides thereof, the compression fluid bag can compress the tendons and suppress the bulge of them, so as to make it possible to make accurate measurements of the living body information.

According to the present invention, it is preferable in the improved invention described above that the auxiliary fluid bags are respectively connected to each other via a division portion having elasticity.

According to this structure, the auxiliary fluid bags can be prevented from separating from each other, achieving good contact intimacy with the arteries. Thus, when the fluid bag is wrapped around e.g. the wrist, it is not easy for the outside-positioned auxiliary fluid bags to mutually separate due to a difference between the inner and outer circumferences, thereby making it possible to make accurate measurements of the living body information.

According to the present invention, it is preferable in the improved invention as described that the auxiliary fluid bags are respectively divided at a substantial center of the compression fluid bag around the living body.

According to this structure, in a tissue of the living body having a tight tissue such as tendons positioned at the substantially central portion and having the arteries positioned on both sides thereof, the auxiliary fluid bags have good contact intimacy with the arteries, making it possible to make accurate measurements of the living body information.

According to the present invention, it is preferable in the improved invention described above that the auxiliary fluid bags cover a substantial center of the compression fluid bag around the living body.

According to this structure, in a tissue of the living body having a tight tissue such as tendons positioned at the substantially central portion and having the arteries positioned on both sides thereof, the auxiliary fluid bags covering the substantial center of the compression fluid bag can compress the tendons and suppress the bulge of them, so that accurate measurements of the living body information can be made.

According to the present invention, it is preferable in the improved invention described above that the auxiliary fluid bags include an auxiliary fluid bag covering the substantial center of the compression fluid bag around the living body together with auxiliary fluid bags positioned on both sides thereof, in which the number of layers of the auxiliary fluid bag covering the substantial center of the compression fluid bag around the living body is larger than the number of layers of the other auxiliary fluid bags.

According to this structure, in a tissue of the living body having a tight tissue such as tendons positioned at the substantially central portion and having the arteries positioned on both sides thereof, the auxiliary fluid bag with the larger number of layers can compress the tendons so as to suppress the bulge of the tendons, so that accurate measurements of the living body information can be made.

According to the present invention, it is preferable in the improved invention described above that the auxiliary fluid bags include an auxiliary fluid bag covering the substantial center of the compression fluid bag around the living body together with other auxiliary fluid bags, in which the length of the auxiliary fluid bag covering the substantial center of the compression fluid bag around the living body is longer than the length of the other auxiliary fluid bags.

According to this structure, in a tissue of the living body having a tight tissue such as tendons positioned at the substantially central portion and having the arteries positioned on both sides thereof, the auxiliary fluid bag with the longer length can compress the tendons so as to suppress the bulge of the tendons, so that accurate measurements of the living body information can be made.

According to the present invention, it is preferable in the improved invention described above that the sensor is a pressure sensor which is provided on an auxiliary fluid bag different from an auxiliary fluid bag for allowing the fluid to flow thereinto.

According to this structure, noise at the time of allowing the fluid to flow into the fluid bag is not easily transmitted to the pressure sensor, so that accurate measurements of the living body information can be made.

BRIEF DESCRIPTION OF DRAWINGS

FIG. 3A is a cross-sectional view of a blood pressure monitor cuff of the blood pressure monitor, while

FIG. 5A is a cross-sectional view of the blood pressure monitor cuff with a division portion, while

BEST MODE FOR CARRYING OUT THE INVENTION

Figure 1:
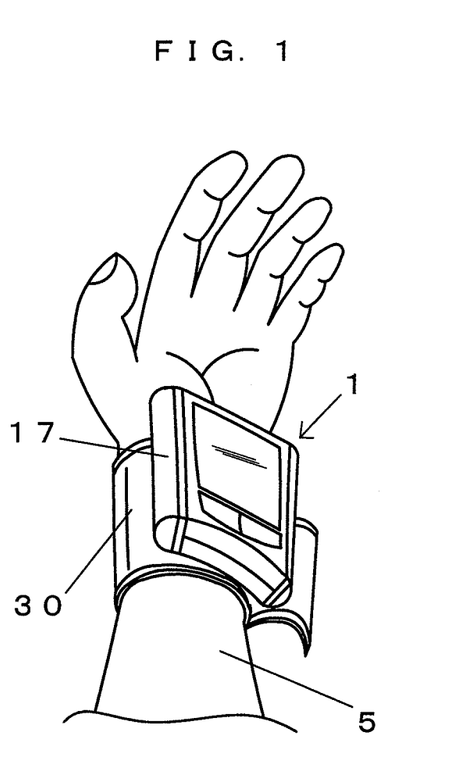
FIG. 1 is an oblique view showing a state where a blood pressure monitor according to an embodiment of the present invention is attached to a wrist.
Figure 2:
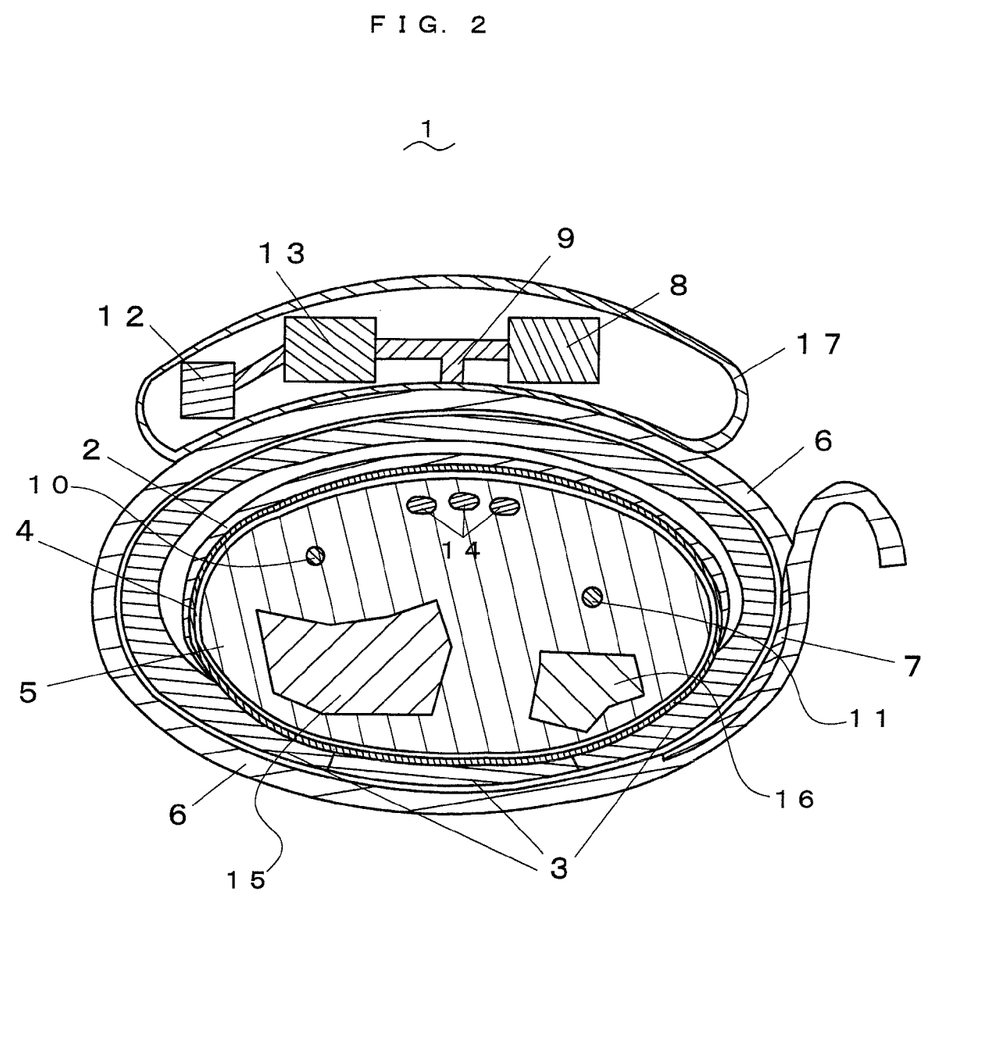
FIG. 2 is a cross-sectional view showing a state where the blood pressure monitor is attached to the wrist.

Referring to FIG. 1 and FIG. 2, a blood pressure monitor (living body information measuring apparatus) according to an embodiment embodying the present invention will be described. FIG. 1 and FIG. 2 show a state where a blood pressure monitor 1 is attached to a wrist 5. The blood pressure monitor 1 comprises a blood pressure monitor main body 17 with a built-in control unit of the blood pressure monitor 1, and a cuff belt 30 attached to the wrist 5 for compressing arteries. Provided inside the blood pressure monitor main body 17 are a pump 8 for allowing a fluid to flow in, a pressure sensor 13 for detecting a pulse wave signal due to a change in the arteries, an outlet valve 12 for releasing the fluid, and so on which are connected via a tube 9 for supplying and exhausting the fluid to and from the cuff belt 30.

The cuff belt 30 comprises: a band 6 for attaching the blood pressure monitor 1 to the wrist 5; a hook-and-loop fastener 7; an elastic plate 3 for holding the attachment of the blood pressure monitor 1 to the wrist 5; a cuff 2 for measuring blood pressure by compressing the arteries; and an inner cloth 4 having high elasticity. The hook-and-loop fastener 7 fixes the band 6 around the wrist 5. The cuff 2 holds the fluid fed from the pump 8, and compresses the arteries of the wrist 5. Note that the detailed structure of the cuff 2 will be described later. Besides, the cuff 2 is manufactured e.g. by blow-molding, or by e.g. heat-fusing and joining, a sheet-shaped material made from a flexible material such as polyurethane or silicone which has good responsiveness to a pulse wave of the arteries.

The wrist 5 is composed e.g. of a radial bone 15 positioned on the thumb side, an ulnar bone 16 positioned on the little finger side, a radial artery 10, an ulnar artery 11, and tendons 14 which are related to the movements of the wrist 5 and fingers. The radial artery 10 is positioned near the radial bone 15, while the ulnar artery 11 is positioned near the ulnar bone 16. Generally, the radial artery 10 is positioned closer to the surface of the wrist 5 than the ulnar artery 11. When the wrist 5 or fingers are bent, the tendons 14 bulge and become tight.

Next, the operation of the blood pressure monitor 1 attached to the wrist 5 for measuring blood pressure will be described. When the blood pressure measurement starts, the pump 8 provided inside the blood pressure monitor 1 feeds a fluid to the cuff 2 to compress the wrist 5. When the cuff 2 reaches a predetermined pressure, the pump 8 stops. Then, the fluid held in the cuff 2 is exhausted via the outlet valve 12 to reduce the pressure of the cuff 2 at a constant rate. At this time, simultaneously, a pulse wave signal (information of a living body) indicating a change in the arteries of the radial artery 10 and the ulnar artery 11 is captured by the cuff 2, and is converted by the pressure sensor 13, based on the amplitude of the pulse wave signal, to pressure values, from which a systolic blood pressure and a diastolic blood pressure are calculated using a predetermined algorithm.

Figure 3A:
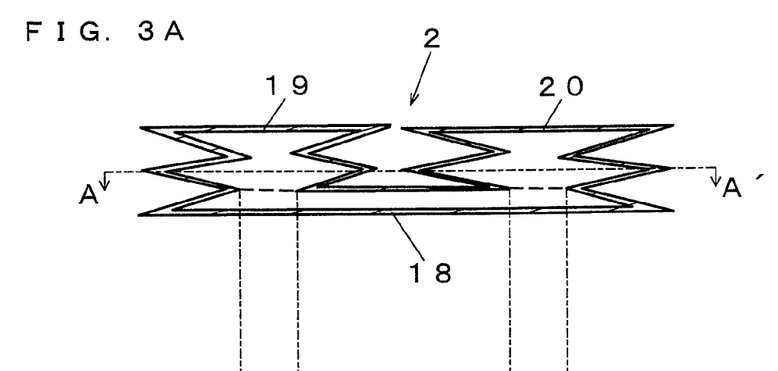
Figure 3B:
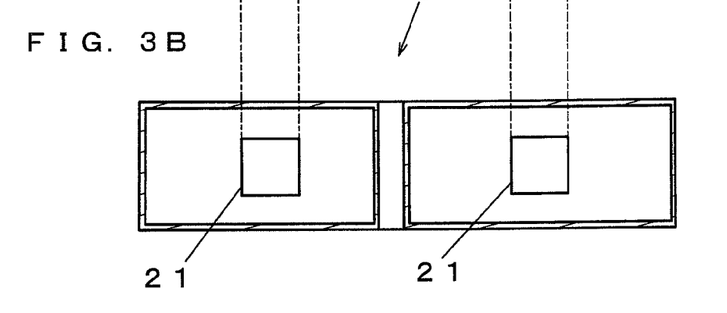
FIG. 3B is a cross-sectional view of FIG. 3A along line A-A'.
Figure 4:
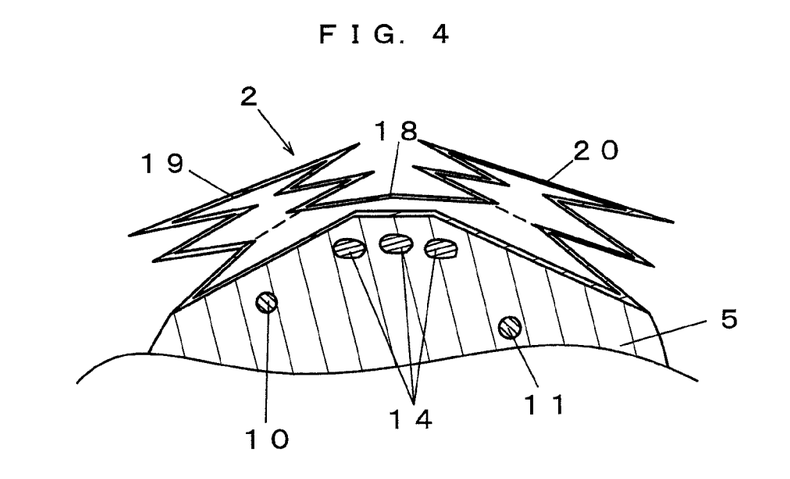
FIG. 4 is a cross-sectional view showing a state where the blood pressure cuff compresses the wrist.
Figure 5A:
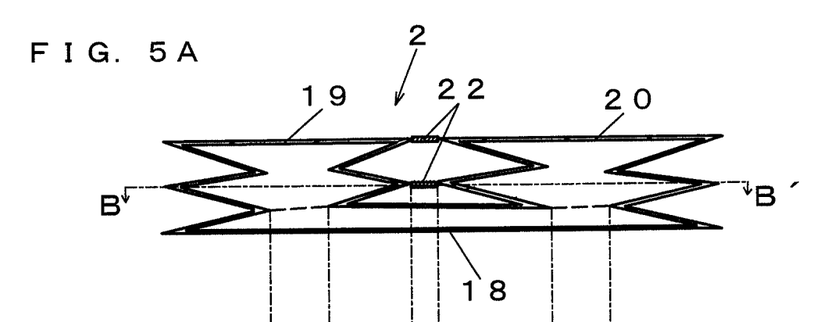
Figure 5B:
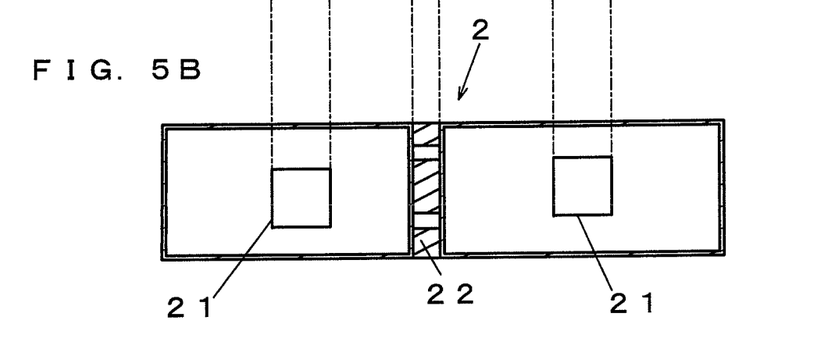
FIG. 5B is a cross-sectional view of FIG. 5A along ling B-B'.

Next, the structure of the cuff 2 will be described with reference to FIG. 3 and FIG. 4. FIG. 4 shows a state where the cuff 2 compresses the wrist 5. In FIG. 4, only the cuff 2 and the wrist 5 are shown for convenience, omitting the showing of the blood pressure monitor main body 17 and others. The cuff 2 is formed of: a compression fluid bag 18 which is provided for detecting a pulse wave signal, and which can be expanded and contracted by being supplied with a fluid; and two auxiliary fluid bags 19, 20 which are provided on an outer side of the compression fluid bag 18, and which can be expanded and contracted by being supplied with the fluid. The auxiliary fluid bags 19, 20 have a two-layer structure, and are connected to the compression fluid bag 18 via opening portions 21. Further, the auxiliary fluid bags 19, 20 are respectively divided from each other.

In the cuff 2 described above, the compression fluid bag 18 compresses the tendons 14, the radial artery 10 and the ulnar artery 11, while the auxiliary fluid bag 19 and the auxiliary fluid bag 20 compress the radial artery 10 and the ulnar artery 11, respectively. Thus, the bulge of the tendons due to the bending of the wrist 5 and fingers can be suppressed, so that the contact intimacy of the compression fluid bag 18 and the auxiliary fluid bags 19, 20 with the wrist 5 is not hindered, making it possible to make accurate measurements of living body information. Further, the length of the compression fluid bag 18 is long to compress the tendons 14, the radial artery 10 and the ulnar artery 11. Thus, even if the cuff 2 is attached at a position shifted from a predetermined attachment position, it has good contact intimacy with the radial artery 10 and the ulnar artery 11, making it possible to make accurate measurements of living body information.

Figure 6:
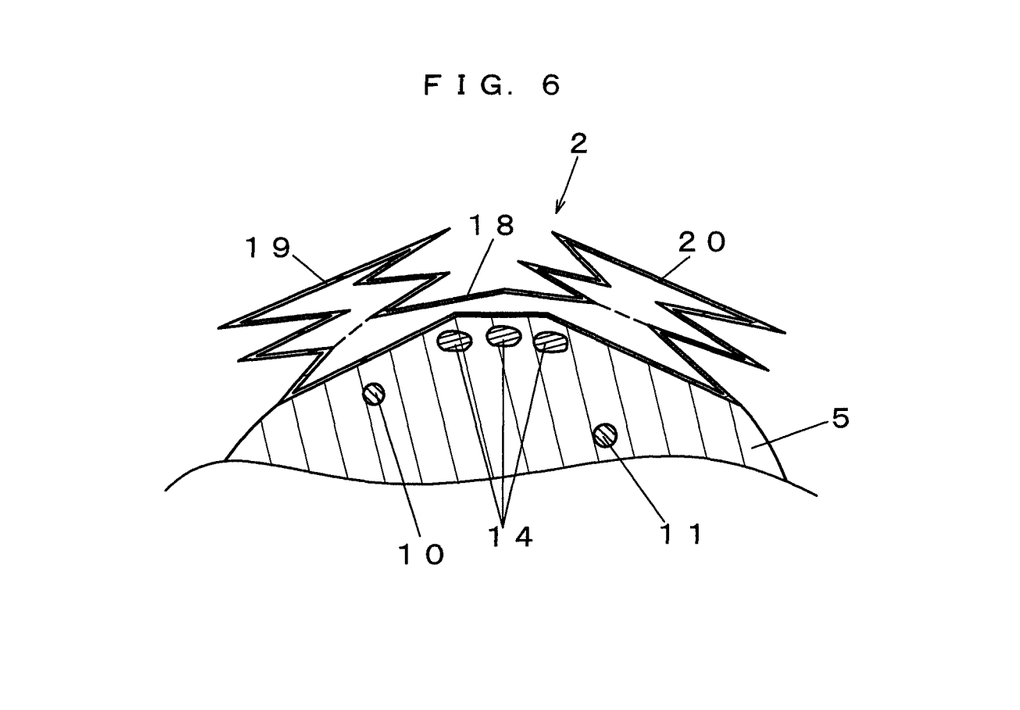
FIG. 6 is a cross-sectional view showing a state where the blood pressure cuff without the division portion compresses a wrist.
Figure 7:
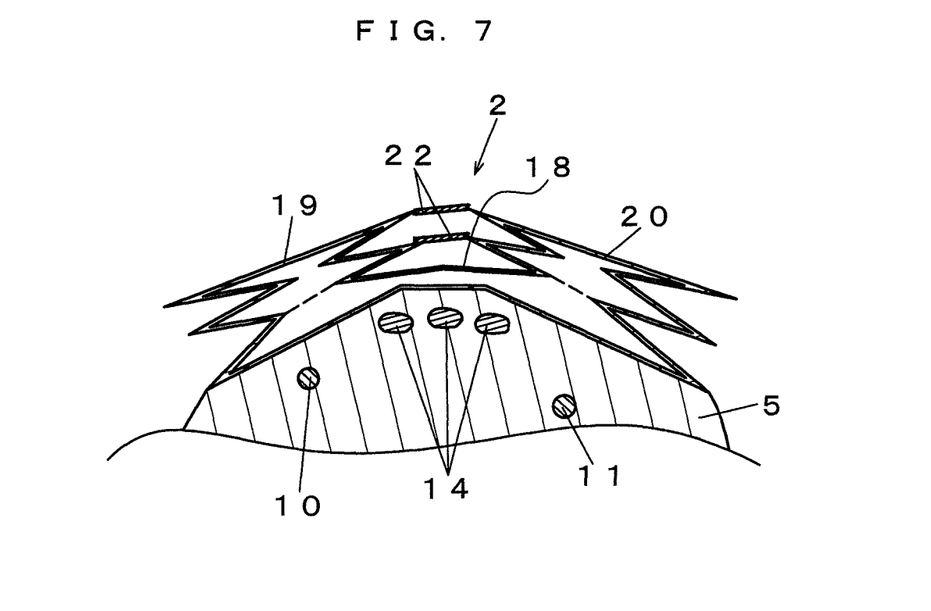
FIG. 7 is a cross-sectional view showing a state where the blood pressure monitor cuff with the division portion compresses the wrist.

Referring next to FIG. 5 to FIG. 13, modified examples of the structures of cuffs 2 will be described. In FIG. 6 to FIG. 10, FIG. 12 and FIG. 13, only a cuff 2 and the wrist 5 are shown for convenience, omitting the showing of the blood pressure monitor main body 17 and others. First, a cuff 2 shown in FIG. 5 and FIG. 7 will be described. FIG. 6 shows a state where a cuff 2 formed of auxiliary fluid bags 19, 20 without a division portion 22 attached thereto compresses the wrist 5. FIG. 7 shows a state where the cuff 2 compresses the wrist 5. In the cuff 2, the auxiliary fluid bag 19 and the auxiliary fluid bag 20 are connected to each other via a division portion 22 having elasticity. The other structure is the same as the structure of FIG. 3 described above.

The wrist 5 has a substantially circular-shaped cross section, so that when a cuff 2 is attached to the wrist 5, there occurs a difference between an inside length and an outside length of the cuff 2. Thus, as shown in FIG. 6, the auxiliary fluid bag 19 and the auxiliary fluid bag 20 may be expanded too much left and right, causing their contact intimacy with the radial artery 10 and the ulnar artery 11 to be poor, and also causing the direction of compressing the auxiliary fluid bag 19 and the auxiliary fluid bag 20 to be shifted from a predetermined direction, so that in some cases it may not be possible to properly compress the radial artery 10 and the ulnar artery 11. For this reason, the auxiliary fluid bags 19, 20 are provided with a division portion 22, whereby even when the cuff 2 is attached to the wrist 5, it is possible to compress the radial artery 10 and the ulnar artery 11 in a proper direction, thereby making it possible to make accurate measurements of living body information.

Figure 8:
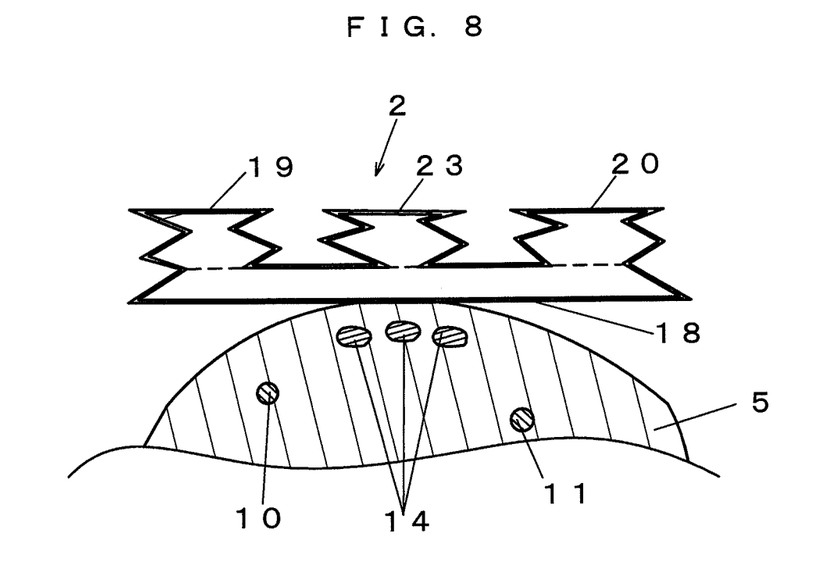
FIG. 8 is a cross-sectional view showing a modified example of the blood pressure monitor cuff.

Next, a cuff 2 shown in FIG. 8 will be described. In this cuff 2, an auxiliary fluid bag 23 is provided between the auxiliary fluid bag 19 and the auxiliary fluid bag 20. The other structure is the same as the structure of FIG. 3 described above. When this cuff 2 is attached to the wrist 5, the auxiliary fluid bag 23 compresses the tendons 14 positioned at a substantially central portion of the wrist 5, making it possible to suppress the bulge of the tendons 14, while at the same time the auxiliary fluid bags 19, can compress the radial artery 10 and the ulnar artery 11, so that accurate measurements of living body information can be made.

Figure 9:
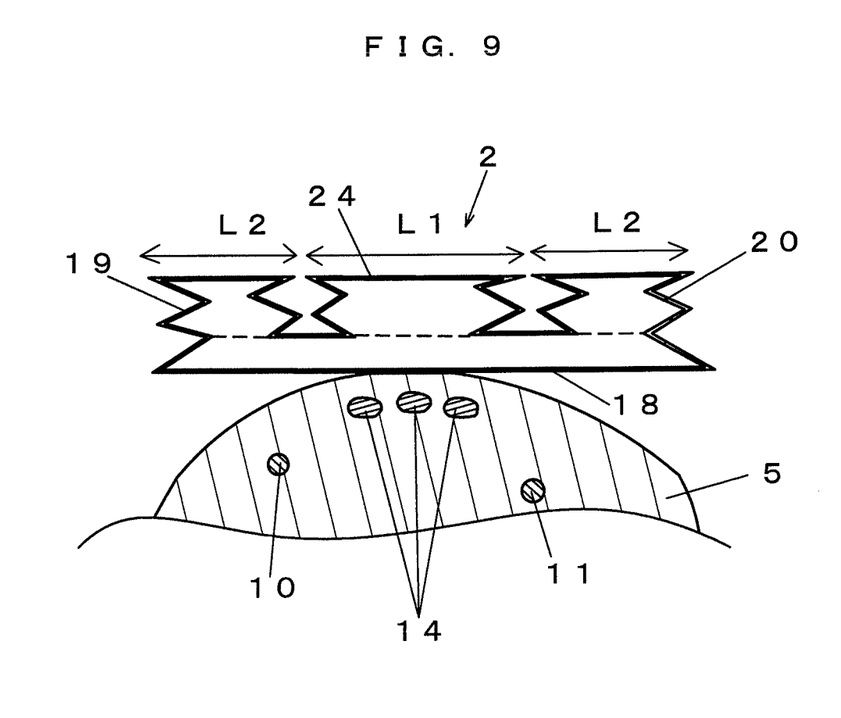
FIG. 9 is a cross-sectional view showing a further modified example of the blood pressure monitor cuff.

Next, a cuff 2 shown in FIG. 9 will be described. In this cuff 2, an auxiliary fluid bag 24 is provided between the auxiliary fluid bag 19 and the auxiliary fluid bag 20, in which the length L1 of the auxiliary fluid bag 24 is longer than the length L2 of the auxiliary fluid bags 19, 20. The other structure is similar to the structure of FIG. 8 described above. When this cuff 2 is attached to the wrist 5, the auxiliary fluid bag 24 further compresses the tendons 14 positioned at the substantially central portion of the wrist 5, making it possible to suppress the bulge of the tendons 14, while at the same time the auxiliary fluid bags 19, 20 can compress the radial artery 10 and the ulnar artery 11, so that accurate measurements of living body information can be made.

Figure 10:
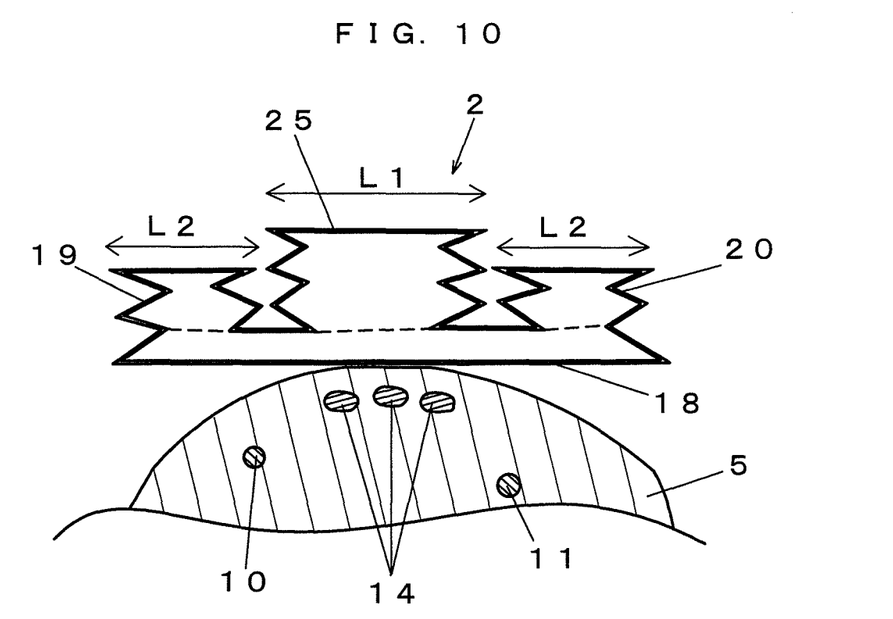
FIG. 10 is a cross-sectional view showing a further modified example of the blood pressure monitor cuff.

Next, a cuff 2 shown in FIG. 10 will be described. In this cuff 2, an auxiliary fluid bag 25 is provided between the auxiliary fluid bag 19 and the auxiliary fluid bag 20, in which the number of layers of the auxiliary fluid bag 25 is larger than the number of layers of the auxiliary fluid bags 19, 20. The other structure is similar to the structure of FIG. 9 described above. When this cuff 2 is attached to the wrist 5, the auxiliary fluid bag 25 further compresses the tendons 14 positioned at the substantially central portion of the wrist 5, making it possible to suppress the bulge of the tendons 14, while at the same time the auxiliary fluid bags 19, 20 can compress the radial artery 10 and the ulnar artery 11, so that accurate measurements of living body information can be made.

Figure 11:
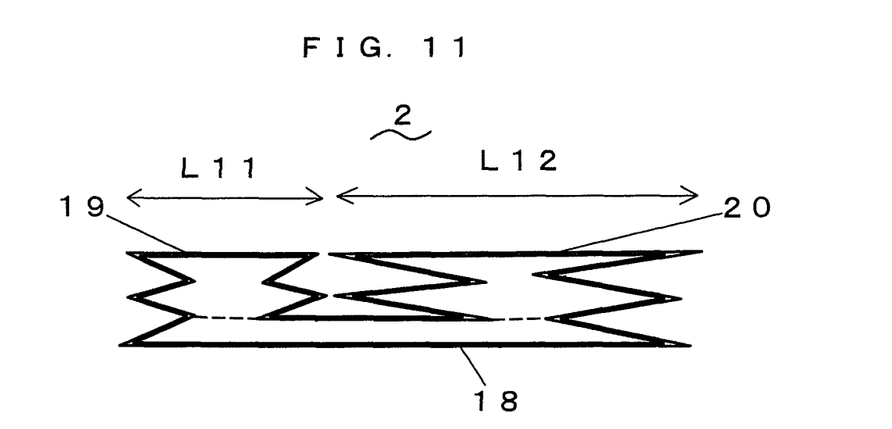
FIG. 11 is a cross-sectional view showing a further modified example of the blood pressure monitor cuff.
Figure 12:
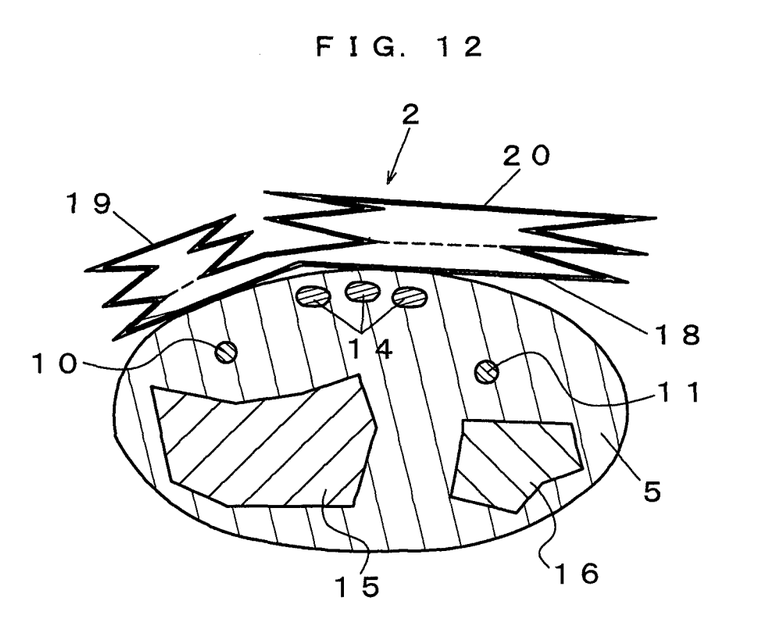
FIG. 12 is a cross-sectional view showing a state where the blood pressure monitor cuff compresses a wrist.

Next, a cuff 2 shown in FIG. 11 and FIG. 12 will be described. In this cuff 2, the length L12 of the auxiliary fluid bag 20 is made longer than the length L11 of the auxiliary fluid bag 19, while the auxiliary fluid bag 20 has a predetermined length to cover at least a substantial center of the wrist 5. The other structure is similar to the structure shown in FIG. 3 described above. When this cuff 2 is attached to the wrist 5, the auxiliary fluid bag 20 compresses the tendons 14 positioned at the substantially central portion of the wrist 5, making it possible to suppress the bulge of the tendons 14, while at the same time the auxiliary fluid bags 19, 20 can compress the radial artery 10 and the ulnar artery 11, so that accurate measurements of living body information can be made.

Further, the ulnar artery 11 is located deeper from the surface of the wrist 5 than the radial artery 10, while the cross-sectional area of the radial bone 15 is larger than the cross-sectional area of the ulnar bone 16, so that the wrist 5 may not be left-right symmetrical at the substantially central portion in some cases. Thus, it may not always be suitable for the auxiliary fluid bags 19, 20 to be left-right symmetrical at the substantially central portion of the cuff 2. Since the auxiliary fluid bag 20 has a predetermined length to cover at least the substantial center of the wrist 5, it can assist the force to compress the tendons 14, and can compress the ulnar artery 11, making it possible to make accurate measurements of living body information for a left-right unsymmetrical living body part.

Figure 13:
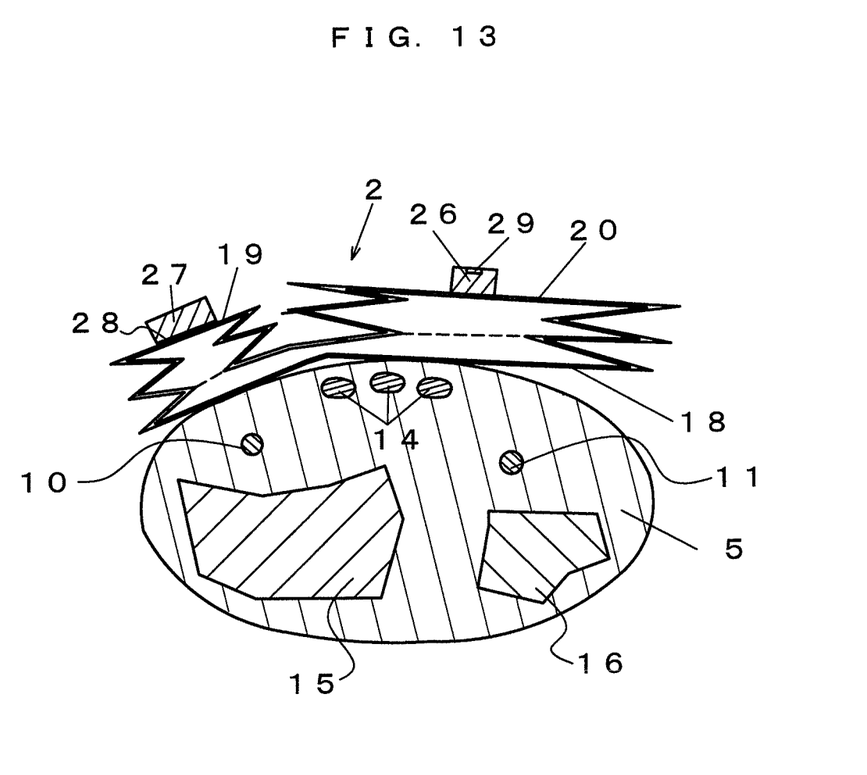
FIG. 13 is a cross-sectional view showing a state where a modified example of the blood pressure monitor cuff compresses a wrist.

Next, a cuff 2 shown in FIG. 13 will be described. In this cuff 2, a pressure sensor 27 is provided on the auxiliary fluid bag 19, while a pump 26 is provided on the auxiliary fluid bag 20 for allowing a fluid to flow thereinto. The other structure is similar to the structure shown in FIG. 12 described above. The vibration of the pump 26 must go through the auxiliary fluid bag 20 and the compression fluid bag 18 before being transmitted to the pressure sensor 27, so that the vibration of the pump 26 is not easily transmitted to the pressure sensor 27, making it possible to make accurate measurements. Note that noise can be further reduced if the size of an inlet hole 29 to allow the fluid to flow in is smaller than a connecting portion 28 between the pressure sensor 27 and the auxiliary fluid bag 19.

In the blood pressure monitor 1 of the embodiment described above, the cuff 2 can suppress the bulge of the tendons 14, so that it is not easy for a user to bend the wrist or fingers inward or outward. Thus, it is not necessary to provide the cuff 2 with a control jig for controlling the postures of the wrist and fingers when measuring the blood pressure, and it is not necessary to limit the posture of the user for measurement, making it easier for the user to use it. In addition, the compression fluid bag 18 is not divided left and right, so that it can adapt to the shift of the attachment position of the cuff 2 and to variations in structure e.g. of the wrist of the user. This makes it possible to make accurate measurements of living body information, and makes it easier for the user to it.

Note that that the present invention is not limited to the structures of the embodiments described above, and various modifications are possible within the scope which does not change the spirit the present invention. For example, although the pressure sensor 27 has been used as a sensor to measure blood pressure, it is not limited thereto and can be any sensor which can detect a change in the arteries. In addition, the embodiments described above has shown an example in the case where the blood pressure monitor is attached to the wrist 5, but it is not limited thereto, and can be attached to another such as finger, ankle, upper arm and neck as well.

This application is based on Japanese patent application 2005-337571, the content of which is to be consequently incorporated into the present invention by reference to the specification and drawings of the above-described patent application.

The present invention has been sufficiently described using presently preferred embodiments with reference to the attached drawings, but it may be obvious to those ordinarily skilled in the art that various alterations and modifications are possible. Accordingly, such alterations and modifications do not depart from the scope of the present invention, and should be interpreted to be included within the scope of the present invention.

The invention claimed is:

1. A living body information measuring apparatus having a fluid bag to compress a living body and a sensor to detect a change in multiple arteries present in a tissue of the living body compressed by the fluid bag for measuring living body information of the living body, the apparatus adapted for engaging a circumference of a portion of the living body and comprising:
   the fluid bag comprising:
   a compression fluid bag configured to contact the living body to measure the living body information from the arteries, wherein the compression fluid bag is configured to expand and contract when supplied with a fluid; and
   at least two independent auxiliary fluid bags which are connected to the compression fluid bag via opening portions, and which are expanded and contracted when supplied with the fluid, wherein the compression fluid bag is configured to engage a circumference of a wrist wherein the at least two auxiliary fluid bags are located on a side of the compression fluid bag opposite the wrist, the auxiliary fluid bags are respectively divided from each other, and when the living body information measuring apparatus is configured to engage a circumference of a wrist, the compression fluid bag is configured to compress tendons positioned at a central portion of the wrist and arteries positioned on both sides of the tendons, and the auxiliary fluid bags are configured to compress the arteries positioned on the both sides of the tendons, respectively.

2. The living body information measuring apparatus according to claim 1, wherein the auxiliary fluid bags are respectively connected to each other via a division portion having elasticity.

3. The living body information measuring apparatus according to claim 2, wherein the auxiliary fluid bags are respectively divided at a center of the compression fluid bag for placement around the living body.

4. The living body information measuring apparatus according to claim 2, wherein the auxiliary fluid bags cover a center of the compression fluid bag for placement around the living body.

5. The living body information measuring apparatus according to claim 1, wherein the auxiliary fluid bags include an auxiliary fluid bag covering a center of the compression fluid bag for placement around the living body together with auxiliary fluid bags positioned on each side of the auxiliary fluid bag covering a center of the compression fluid bag, in which the auxiliary fluid bag covering the center of the compression fluid bag for placement around the living body has a larger number of layers than the auxiliary fluid bags positioned on each side of the auxiliary fluid bag covering the center of the compression fluid bag.

6. The living body information measuring apparatus according to claim 4, wherein the auxiliary fluid bags include an auxiliary fluid bag covering the center of the compression fluid bag for placement around the living body together with other auxiliary fluid bags, in which a length of the auxiliary fluid bag covering the center of the compression fluid bag for placement around the living body is longer than a length of the other auxiliary fluid bags on each side of the auxiliary fluid bag covering the center of the compression fluid bag.

7. The living body information measuring apparatus according to claim 1, wherein the sensor is a pressure sensor which is provided on an auxiliary fluid bag different from an auxiliary fluid bag into which the fluid flows.

8. The living body information measuring apparatus according to claim 2, wherein the auxiliary fluid bags include an auxiliary fluid bag covering a center of the compression fluid bag for placement around the living body together with auxiliary-fluid bags positioned on each side of the auxiliary-fluid bag covering a center of the compression fluid bag, in which the auxiliary fluid bag covering the center of the compression fluid bag for placement around the living body a larger number of layers than the auxiliary fluid bags positioned on each side of the auxiliary fluid bag covering the center of the compression fluid bag.

9. The living body information measuring apparatus according to claim 1, wherein each of the at least two independent auxiliary fluid bags comprises a distinct accordion fold structure.

10. The living body information measuring apparatus according to claim 1, the compression fluid bag, when attached to the living body, is configured to be positioned opposite tendons and each of the at least two independent auxiliary fluid bags are configured to be positioned opposite arteries of the living body.

* * * * *